United States Patent
Voelkel et al.

(10) Patent No.: US 8,426,596 B2
(45) Date of Patent: Apr. 23, 2013

(54) PROCESS OF PRODUCING BLEACH BOOSTERS

(75) Inventors: Ludwig Voelkel, Limburgerhof (DE); Christian Bittner, Bensheim (DE); Ingo Muenster, Boehl-Iggelheim (DE); Frank Dietsche, Schriesheim (DE); Wolfgang Schrof, Neuleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 13/224,621

(22) Filed: Sep. 2, 2011

(65) Prior Publication Data

US 2011/0319622 A1 Dec. 29, 2011

Related U.S. Application Data

(62) Division of application No. 11/917,217, filed as application No. PCT/EP2006/063238 on Jun. 14, 2006, now Pat. No. 8,129,531.

(30) Foreign Application Priority Data

Jun. 17, 2005 (EP) .................................... 05013129
Jun. 17, 2005 (EP) .................................... 05013134

(51) Int. Cl.
*C07D 217/10* (2006.01)
(52) U.S. Cl.
USPC ....................................................... 546/151
(58) Field of Classification Search .................. None
See application file for complete search history.

(56) References Cited

FOREIGN PATENT DOCUMENTS

WO         01 16273         3/2001
WO         2007 001261         1/2007

*Primary Examiner* — Zinna Northington Davis
(74) *Attorney, Agent, or Firm* — Oblon, Spivak, McClelland, Maier & Neustadt, L.L.P.

(57) ABSTRACT

This invention relates to a process of producing compounds, which are useful as bleach boosters, as well as to the compounds, which are obtainable using said process, and to their use.

22 Claims, No Drawings

PROCESS OF PRODUCING BLEACH BOOSTERS

CROSS REFERENCE TO RELATED APPLICATIONS

The present application is a divisional application based on U.S. application Ser. No. 11/917,217 filed Dec. 12, 2007, now U.S. Pat. No. 8,129,531, which published on Sep. 4, 2008, as US 2008/0214819 A1, as the national stage of international application PCT/EP2006/063238, filed on Jun. 14, 2006, claiming benefit to the filing date of European Appl. No. 2005 013129.1 and 2005 013134.1, both filed on Jun. 17, 2005. All of the above applications are hereby incorporated by reference in their entirety.

This invention relates to a process of producing compounds, which are useful as bleach boosters, as well as to the compounds, which are obtainable using said process, and to their use.

Oxygen bleaching agents, for example hydrogen peroxide, are typically used to facilitate the removal of stains and soils from clothing and various surfaces. Unfortunately such agents are extremely temperature rate dependent. As a result, when such agents are employed in colder solutions, the bleaching action of such solutions is markedly decreased.

In an effort to resolve the aforementioned performance problem, the industry developed a class of materials known as "bleach activators" or "bleach boosters", with both terms being used identical. However, as such materials rapidly lose their effectiveness at solution temperatures of less than 40° C., new organic catalysts such as 3,4-dihydro-2-[2-(sulfooxy)decyl]isoquinolimium, inner salt were developed. The term "organic catalyst" is used as another term for "bleach activator" or "bleach booster" throughout this description. In general, while such current art catalysts are effective in lower temperature water conditions, they can inactivate certain enzymes. As most laundry and cleaning compositions are formulated with enzymes, formulating cleaning products with such catalysts can be problematic.

Accordingly, there is a need for an organic catalyst that can provide the combined benefits of formulation flexibility, low water temperature bleaching performance and enzyme compatibility.

The process of producing 1-(4,4-dimethyl-3,4-dihydroisochinoline)decane-2-sulfate, which is known to be a bleach booster, is described in WO 01/16273:
1,2-decanediol is dissolved in carbon tetrachloride. Thionyl chloride is added dropwise at room temperature and the reaction mixture is heated to 60° C. After some h time the reaction mixture is cooled using an ice bath. Water and acetonitrile are added as well as ruthenium chloride hydrate and sodium periodate. After stirring for an hour at room temperature, the reaction mixture is extracted with diethylether (4 times); the organic layers are subsequently washed with water (5 times), saturated sodium bicarbonate (3 times), brine (2 times), filtered through celite/silica gel, and dried over magnesium sulphate. After that the resulting liquid is concentrated to yield a clear oil, which oil is 1,2-decanediol cyclic sulphate. In the next reaction step 4,4-dimethyl-3,4-dihydroisoquinoline and acetonitrile are combined with the 1,2-decanediol cyclic sulphate, which is added in one portion. After another addition of acetonitrile the reaction mixture is stirred for some h. Then the precipitate is collected, washed with acetone and allowed to dry to give 1-(4,4-dimethyl-3,4-dihydroisochinoline)decane-2-sulfate.

While this process can be used in laboratory scale there exists a strong need to have a process that is usable in industrial scale, i.e. a process, which avoids the use of expensive educts such as thionyl chloride. Therefore it is one goal of the present invention to find a process, which avoids the use of thionyl chloride. It is another goal of the present invention to find new compounds, which are accessible using this process and which compounds can be used as bleach boosters, preferably those bleach boosters having the combined benefits as are outlined above.

Surprisingly it has been found that these needs are met by the compounds according to embodiments 1 to 6 and the process according to embodiments 7 to 22, as follows:

1.) Compound of formula (I) or (II)

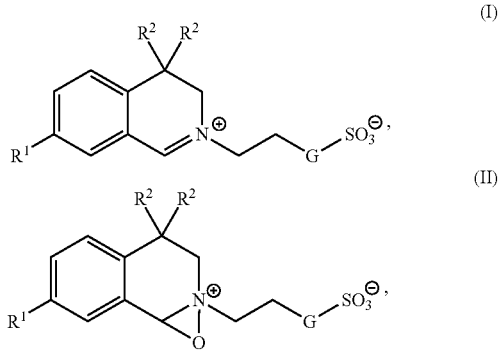

wherein $R^1$, $R^2$ and G independently from each other are selected from
$R^1$=H, $C_1$-$C_{20}$-alkyl, $C_1$-$C_{20}$-cycloalkyl, $C_1$-$C_{20}$-aryl or $C_2$-$C_{20}$-aralkyl,
$R^2$=$C_1C_{20}$-alkyl, $C_1$-$C_{20}$—cycloalkyl, $C_1$-$C_{20}$-aryl or $C_1$-$C_{20}$-aralkyl and
G=-O—, —$CH_2$O—, —$CH_2$—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—.

2.) Compound according to embodiment 1, wherein $R^1$, $R^2$ and G independently from each other are selected from
$R^1$=H, $C_1$-$C_{12}$-alkyl, $C_1$-$C_{12}$-cycloalkyl, $C_1$-$C_{12}$-aryl or $C_1$-$C_{12}$-aralkyl,
$R^2$=$C_1$-$C_{12}$-alkyl, $C_1$-$C_{12}$-cycloalkyl, $C_1$-$C_{12}$-aryl or $C_1$-$C_{12}$-aralkyl and
G=-O—, —$CH_2$O—, —($CH_2$)$_2$—, —$CH_2$—, —($CH_2$)$_3$—, —($CH_2$)$_4$—, —($CH_2$)$_5$—.

3.) Compound according to embodiment 1 or 2, wherein $R^1$, $R^2$ and G independently from each other are selected from
$R^1$=H, $C_1C_4$-alkyl, $C_1C_6$-cycloalkyl, $C_1C_8$-aryl or $C_1C_8$-aralkyl,
$R^2$=$C_1C_4$-alkyl, $C_1C_6$-cycloalkyl, $C_1C_8$-aryl or $C_1C_8$-aralkyl and
G=-$CH_2$—.

4.) Compound according to any one of embodiment 1, 2 or 3, wherein G is selected from the group consisting of: n-butyl, n-pentyl, cyclopentyl, n-hexyl, cyclohexyl, n-heptyl, cyclohexylmethyl, n-octyl, benzyl, 2-methylbenzyl, 3-methylbenzyl, 4-methylbenzyl, 4-ethylbenzyl, 4-iso-proylbenzyl and 4-tert-butyl-benzyl.

5.) Compound according to any one of embodiments 1 to 4, having an enzyme compatibility value of 70 or greater.

6.) Compound according to embodiment 5, having an enzyme compatibility value of 80 or greater.

7.) Process comprising the following steps:
bisalkylation of a benzene cyanide,
reduction of the nitrile obtained in step a) to give an amine,
amidification of the amine obtained in step b),
ring closure of the product obtained in step c),
quaternation of the product obtained in step d).

8.) Process according to embodiment 7, wherein in step a) an alkylchloride, -bromide, -iodide or -tosylate or a substituted arylchloride, -bromide, -iodide or -tosylate is used in amount of 2 to 4 equivalents based on benzylcyanide.

9.) Process according to embodiment 8, wherein in step a) an alkylchloride or substituted benzylchloride is used in amount of 2 to 2.5 equivalents based on benzylcyanide.

10.) Process according to embodiment 7 to 9, wherein the reaction of step a) takes place in the presence of 2 to 4 equivalents (based on benzylcyanide) of a base.

11.) Process according to embodiment 10, wherein the base is KOtBu or KOH/tBuOH.

12.) Process according to any one of embodiments 7 to 11, wherein solvent, alkylating agent and benzylcyanide are first mixed and the reaction is initiated by addition of the base.

13.) Process according to any one of embodiments 7 to 12, wherein step b) is performed using hydrogen in the presence of a catalyst.

14.) Process according to any one of embodiments 7 to 13, wherein step c) is performed using formic acid and/or formic acid ester.

15.) Process according to any one of embodiments 7 to 14, wherein step d) is performed using phosphorous pentoxide and an acid.

16.) Process according to embodiment 15, wherein the acid is selected from the group consisting of poly phosphorous acid, trifluormethaneacid, formic acid and methane sulfonic acid.

17.) Process according to embodiment 15 or 16, wherein the reaction mixture of step d) is neutralized using KOH.

18.) Process according to any one of embodiments 7 to 17, wherein in step d) after neutralization the amine is oxidized to give an imine using sodium hypochlorite.

19.) Process according to any one of embodiments 7 to 18, wherein in step the alkylating agent is used in an amount of 1 to 1.2 equivalents based on the product from step d).

20.) Process according to any one of embodiments 7 to 19 wherein in at least one of steps a) to e) a solvent is used.

21.) Process according to embodiment 20, wherein the same solvent is used in more than one step.

22.) Process according to embodiment 20 or 21, wherein the solvent is toluene.

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including anti-bacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . ." means that moieties or elements that are selected from the referenced Markush group can be the same, can be different or any mixture of elements.

The test methods disclosed in the Test Methods Section of the present application must be used to determine the respective values of the parameters of Applicants' inventions.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

A Compound of formula (I) or (II)

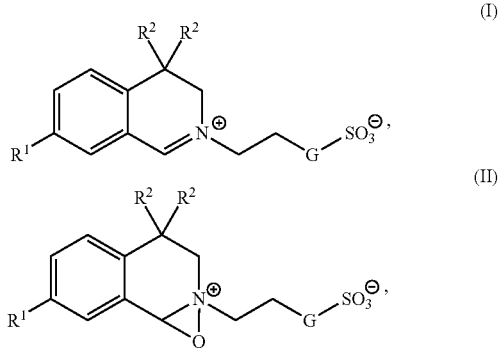

wherein $R^1$, $R^2$ and G independently from each other are selected from
$R^1$=H, $C_1$-$C_{20}$-alkyl, such as $C_1$-, $C_2$-, $C_3$-, $C_4$-, $C_5$-, $C_6$-, $C_{19}$-, $C_{20}$-alkyl, $C_1$-$C_{20}$-cy-cloalkyl, such as, $C_5$-, $C_6$-, $C_7$-, $C_8$-, $C_{19}$-, $C_{20}$-cycloalkyl, $C_1$-$C_{20}$-aryl, such as $C_5$-, $C_6$-, $C_7$-, $C_8$-, $C_{19}$-, $C_{20}$-aryl or $C_1$-$C_{20}$-aralkyl,
$R^2$=$C_1$-$C_{20}$-alkyl, $C_1$-$C_{20}$-cycloalkyl, $C_1$-$C_{20}$-aryl or $C_1$-$C_{20}$-aralkyl and
G=-O—, —$CH_2O$—, —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$— forms an object of the present invention.

A compound as mentioned above, wherein
$R^1$, $R^2$ and G independently from each other are selected from
$R^1$=H, $C_1$-$C_{12}$-alkyl, $C_1$-$C_{12}$-cycloalkyl, $C_1$-$C_{12}$-aryl or $C_1$-$C_{12}$-aralkyl,
$R^2$=$C_1$-$C_{12}$-alkyl, $C_1$-$C_{12}$-cycloalkyl, $C_1$-$C_{12}$-aryl or $C_1$-$C_{12}$-aralkyl and
G=-O—, —$CH_2O$—, —$(CH_2)_2$—, —$CH_2$—, —$(CH_2)_3$—, —$(CH_2)_4$—, —$(CH_2)_5$— is preferred.

A compound as mentioned above, wherein
$R^1, R^2$ and G independently from each other are selected from
$R^1$=H, $C_1$-$C_4$-alkyl, $C_1$-$C_6$-cycloalkyl, $C_1$-$C_8$-aryl or $C_1$-$C_8$-aralkyl,
$R^2$=$C_1$-$C_4$-alkyl, $C_4$-$C_8$-alkyl, $C_1$-$C_6$-cycloalkyl, $C_1$-$C_8$-aryl or $C_1$-$C_8$-aralkyl and
G=-$CH_2$— is more preferred.

A compound as mentioned above, wherein
G is selected from the group consisting of: n-butyl, n-pentyl, cyclopentyl, n-hexyl, cyclohexyl, n-heptyl, cyclohexylmethyl, n-octyl, benzyl, 2-methylbenzyl, 3-methylbenzyl, 4-methylbenzyl, 4-ethylbenzyl, 4-iso-propylbenzyl and 4-tert-butylbenzyl forms a particularly preferred embodiment of the present invention.

Suitable $C_1$-$C_4$ alkyl moieties include, but are not limited to methyl, ethyl, iso-propyl, and tert-butyl. Those compounds in which at least one of $R^1$, $R^2$ is methyl, ethyl, iso-propyl, and tert-butyl are preferred.

Each $R^2$ preferably is independently selected from $C_4$-$C_8$ alkyl, $C_1$-$C_{12}$-cycloalkyl, benzyl, 2-methylbenzyl, 3-methylbenzyl, 4-methylbenzyl, 4-ethylbenzyl, 4-iso-propylbenzyl and 4-tert-butylbenzyl. Suitable $C_4$-$C_8$ alkyl moieties include, but are not limited to n-butyl, n-pentyl, n-hexyl, n-heptyl and octyl. $C_1$-$C_{12}$-cycloalkyl includes cyclohexyl, cyclopentyl, cyclohexylmethyl.

In one aspect of the invention G is selected from —O— and —$CH_2$—. $R^1$ is selected from H, methyl, ethyl, iso-propyl, and tert-butyl. Each $R^2$ is independently selected from $C_4$-$C_6$ alkyl, benzyl, 2-methylbenzyl, 3-methylbenzyl, and 4-methylbenzyl.

In one aspect of the invention G is —$CH_2$—, $R^1$ is H and each $R^2$ is independently selected from n-butyl, n-pentyl, n-hexyl, benzyl, 2-methylbenzyl, 3-methylbenzyl, and 4-methylbenzyl.

Surprisingly it was found that the compounds of the present invention lead to better low water temperature bleaching performance, when used in a cleaning composition.

In addition to that the unexpected effect of good enzyme compatibility was found. Applicants have found that judicious selection of the $R^1$ and $R^2$ moieties of the organic catalyst of the present invention results in improved enzyme compatibility. While not being bound by theory, Applicants believe this is due to favourable partitioning of the catalyst in aqueous environments as a result of the aforementioned judicious selection of the said moieties.

In one aspect of Applicants' invention, the organic catalyst has an enzyme compatibility value of 70 or greater, or even 80 or greater. Typical enzymes that are used in cleaning compositions include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

Cleaning compositions and cleaning composition additives comprising the compounds described in detail above may be advantageously employed for example, in laundry applications, hard surface cleaning, automatic dishwashing applications, as well as cosmetic applications such as dentures, teeth, hair and skin. However, due to the unique advantages of both increased effectiveness in lower temperature solutions and the superior enzyme compatiblity, the organic catalysts of the present invention are ideally suited for laundry applications such as the bleaching of fabrics through the use of bleach containing detergents or laundry bleach additives. Furthermore, the organic catalysts of the present invention may be employed in both granular and liquid compositions.

The organic catalysts of the present invention may also be employed in a cleaning additive product. While the additive product may be, in its simplest form, Applicants' organic catalyst, a cleaning additive product including the organic catalysts of the present invention is ideally suited for inclusion in a wash process when additional bleaching effectiveness is desired. Such instances may include but are not limited to, low temperature solution cleaning application.

Cleaning compositions and cleaning additives require a catalytically effective amount of Applicants' organic catalyst. The required level of such catalyst may be achieved by the addition of one or more species of Applicants' organic catalyst. As a practical matter, and not by way of limitation, the compositions and cleaning processes herein can be adjusted to provide on the order of at least 0.001 ppm, from about 0.001 ppm to about 500 ppm, from about 0.005 ppm to about 150 ppm, or even from about 0.05 ppm to about 50 ppm of Applicants' organic catalyst in the wash liquor. In order to obtain such levels in the wash liquor, typical compositions herein may comprise from about 0.0002% to about 5%, or even from about 0.001% to about 1.5%, of organic catalyst, by weight of the cleaning compositions.

When the Applicants' organic catalyst is employed in a granular composition, it may be desirable for the Applicants' organic catalyst to be in the form of an encapsulated particle to protect the Applicants' organic catalyst from moisture and/or other components of the granular composition during storage. In addition, encapsulation is also a means of controlling the availability of the Applicants' organic catalyst during the cleaning process and may enhance the bleaching performance of the Applicants' organic catalyst. In this regard, the Applicants' organic catalyst can be encapsulated with any encapsulating material known in the art.

The encapsulating material typically encapsulates at least part, preferably all, of the Applicants' organic catalyst. Typically, the encapsulating material is water-soluble and/or water-dispersible. The encapsulating material may have a glass transition temperature (Tg) of 0° C. or higher.

The encapsulating material is preferably selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. Preferably the encapsulating material is a carbohydrate, typically selected from the group consisting of monosaccharides, oligosaccharides, polysaccharides, and combinations thereof. Most preferably, the encapsulating material is a starch. Preferred starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark Expancel®, and those supplied by PQ Corp. of Valley Forge, Pa. USA under the tradename PM 6545, PM 6550, PM 7220, PM 7228, Extendospheres®, Luxsil®, Q-Cel® and Sphericel®.

The cleaning compositions herein will preferably be formulated such that, during use in aqueous cleaning operations, the wash water will have a pH of between about 6.5 and about 11, or even about 7.5 and 10.5. Liquid dishwashing product formulations may have a pH between about 6.8 and about 9.0.

Laundry products typically have a pH of from about 9 to about 11. Techniques for controlling pH at recommended usage levels include the use of buffers, alkalis, acids, etc., and are well known to those skilled in the art.

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

The cleaning compositions can be formulated into any suitable form and prepared by any process chosen by the formulator, non-limiting examples of which are described in Applicants' examples and in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Organic Catalyst/Enzyme Compatibility Test

The test described below uses an alpha amylase activity assay to measure the impact of organic catalysts on the enzyme.

Equipment. UV/Vis spectrophotometer capable of measuring @ 415 nm, heated magnetic stirrer capable of 40° C., 5 ml Luer lock syringe and filters (Acrodisc 0.45 伐 μm), pH meter, and balance (4-place analytical).

Reagents. Merck Amylase Kit (Merck Eurolab, Cat. No. 1.19718.0001); Trizma Base (Sigma Cat # T-1503, or equivalent); Calcium Chloride Dihydrate (Sigma Cat # C-5080, or equivalent); Sodium Thiosulfate Pentahydrate (Sigma Cat # S-6672 or equivalent); Hydrochloric Acid (VWR Cat # JT9535-0, or equivalent); Hardness solution (CTC Group, 3.00 gr/cc or equivalent); Sodium Percarbonate; Peracetic Acid (Aldrich, Cat. #26933-6 or equivalent); Amylase enzymes: Termamyl, Natalase, and Duramyl (Novozymes, Denmark); Granular detergent matrix containing no enzyme, organic catalyst or bleaching agents.

1.) Solution Preparation: Prepare the Following:
   a.) TRIS Assay Buffer. Prepare 1 liter of 0.1M TRIS buffer, 0.5% sodium thiosulphate (W/V), 0.11% calcium chloride (w/v) at pH 8.3.
   b.) Blank Detergent Solution. Prepare one liter of 0.5% enzyme and bleach free granular detergent product in deionized water (W/V) that is 250 ppm $H_2O_2$ (0.77 gm percarbonate) and 10 gpg hardness (880 UI of hardness).
   c.) Termamyl, Duramyl and Natalase Stock. Make 100 ml solutions each of a 0.1633 mg active Termamyl per ml TRIS Buffer, a 0.1159 mg active Natalase per ml TRIS Buffer, and a 0.1596 mg active Duramyl per ml TRIS Buffer.
   d.) Organic catalyst stocks. Make a 500 ppm in methanol solution of μm.
   e.) Peracetic acid stock. Make a 3955 ppm peracetic acid solution in deionized water.
   f.) Amylase reagent. Follow Merck kit instructions for preparing flacons (containers) 1 and 2 using flacon 3 and subsequent mixing of flacons 1 and 2 to produce the final reagent used in the amylase activity analysis.

2.) Sample Analysis
   a.) Analysis of sample with enzyme only: Add 100 ml of blank detergent solution to a 150 ml beaker. Place beaker on heated stir plate and bring temperature to 40° C. with stirring. Add Y μl of enzyme stock to the beaker where Y=612 μL for Duramyl, 306 μl for Termamyl, or 918 μl for Natalase. Spike only enzyme of interest. Stir sample for 1 minute. Start timer. At 7 minutes 45 seconds, pull a sample and filter it using a 0.45 μm syringe filter (5 ml syringe). Mix 6 μl of filtered sample with 250 μL of amylase reagent in a cuvette and place the cuvette in a UV/VIS spectrophotometer and monitor change in absorbance at 415 nm. Determine length of time ($t_E$) to the nearest second required to obtain an absorbance reading of 1.0 for each enzyme. Use each enzyme's $t_E$ in Steps 2.)b.) and 2.)c.) below.
   b.) Analysis of sample with enzyme and peracetic acid only. Follow Step 2.)a.) except after enzyme addition, allow solution to stir for 1 minute then add 127 μl of peracetic acid stock and start timer. Pull sample at 7 minutes 45 seconds as in Step 2.)a.). Once sample and reagent are mixed, record the absorbance at $t_E$ for the respective enzyme. Designate such absorbance $A_b$.
   c.) Analysis of sample with enzyme, peracetic acid, and organic catalyst. Follow Step 2.)a.) except after enzyme addition, allow solution to stir for 1 minute then add 127 μl of peracetic acid stock and 100 μl of organic catalyst stock and start timer. Pull sample at 7 minutes 45 seconds as in Step 2.)a.). Once sample and reagent are mixed, record the absorbance at $t_E$ for the respective enzyme. Designate such absorbance A, 3.) Calculate Enzyme Compatibility Value (ECV)
   a.) Calculate the ECV for each specific enzyme: termamyl ($ECV_{ter}$), duramyl ($ECV_{dur}$) and natalase ($ECV_{nat}$). The ECV for any specific enzyme is $(A_c/A_b) \times 100$ where $A_b$ and $A_c$ are the values determined in Steps 2.)b.) and 2.)c.), respectively, for that enzyme.
   b.) The ECV for a given organic catalyst is the average of the individual ECV values for the three enzymes. Thus, $ECV=(ECV_{ter}+ECV_{dur}+ECV_{nat})/3$.

The present invention does not only deal with compounds, but also with processes of producing such compounds. Therefore a process comprising the following steps:
   a) bisalkylation of a benzene cyanide,
   b) reduction of the nitrile obtained in step a) to give an amine,
   c) amidification of the amine obtained in step b),
   d) ring closure of the product obtained in step c),
   e) quaternation of the product obtained in step d)
forms another object of the present invention.

The overall process can be illustrated as follows:

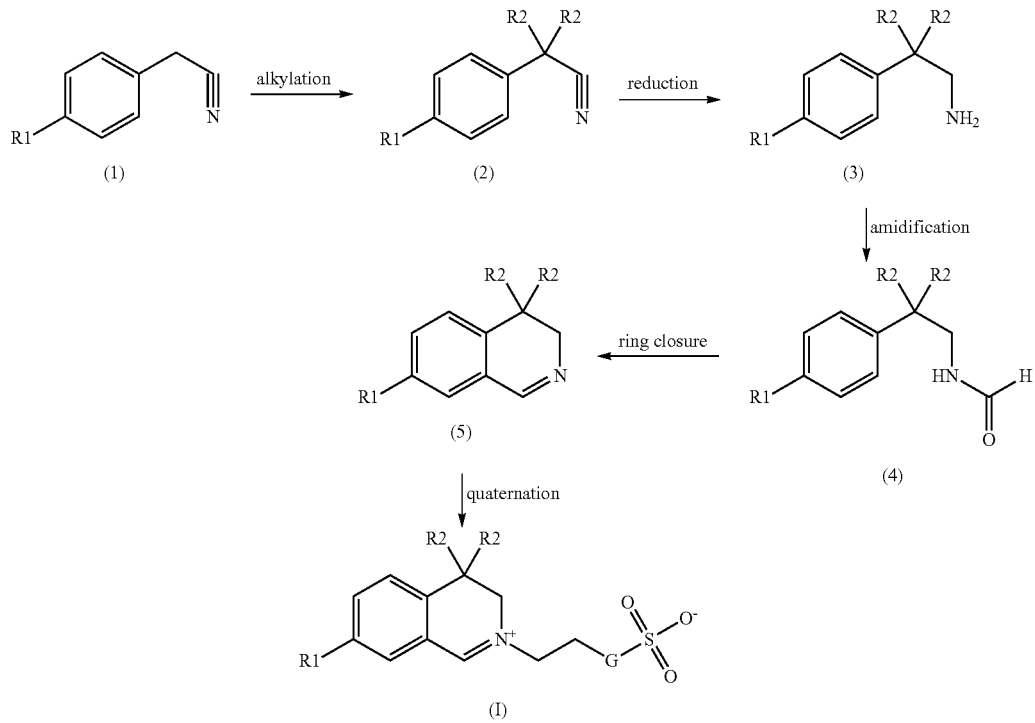

Based on this general process there exist preferred embodiments, one of which is a process, wherein in step a) an alkylchloride, -bromide, -iodide or -tosylate or a substituted arylchloride, -bromide, -iodide or -tosylate is used in amount of 2 to 4 equivalents based on benzylcyanide. A process wherein in step a) an alkylchloride or substituted benzylchloride is used in an amount of 2 to 2.5 equivalents based on benzylcyanide is more preferred.

A process as described above, wherein the reaction of step a) takes place in the presence of 2 to 4 equivalents (based on benzylcyanide) of a base is another preferred embodiment of the present invention, whereby it is preferred when the base is KOtBu or KOH/tBuOH and it is also preferred when solvent, alkylating agent and benzylcyanide are first mixed and the reaction is initiated by addition of the base. By doing this the formation of side products can be reduced.

Possible solvents for the reaction in step a) are toluene, tetrahydrofurane (THF), dimethylsulfoxide (DMSO), dimethylformamide (DMF) and others, with toluene being preferred. The reaction of step a) can be performed at atmospheric pressure as well as under positive pressure or under a light vacuum. The use of a neutral gas is possible. The temperature lies in the range of from −40° C. to 200° C., with a range from 0 to 120° C. being preferred.

A process as described above, wherein step b) is performed using hydrogen in the presence of a catalyst is preferred. When using a borane-THF-complex numerous side products are obtained. When using a catalyst such as Raney-nickel the appearance of such side products can be avoided or at least be reduced and the purity of the product is increased.

Possible solvents for the reaction in step b) again are toluene, tetrahydrofurane (THF), dimethylsulfoxide (DMSO), dimethylformamide (DMF) and others, with toluene being preferred. The reaction of step b) can be performed at about atmospheric pressure as well as under positive pressure, with positive pressure being preferred. The temperature lies in the range of from −40° C. to 200° C., with a range from 0 to 120° C. being preferred.

A process as described above, wherein step c) is performed using formic acid and/or formic acid ester forms another preferred embodiment of the present invention, with the use of formic acid ester being preferred. It is particularly preferred to use formic acid methyl ester, since it has a boiling point of 34° C., which makes the removal of a surplus easier compared to formic acid having a boiling point of 100° C. The reaction of step c) can advantageously be performed at a temperature of about room temperature. In any case it should be performed below the boiling temperature of the components. By increasing the pressure, which normally is atmospheric pressure, also the temperature can be increased, which leads to a reduction of the time needed for the completion of the reaction.

Step d) can be performed using a Bischler-Napieralski reaction:

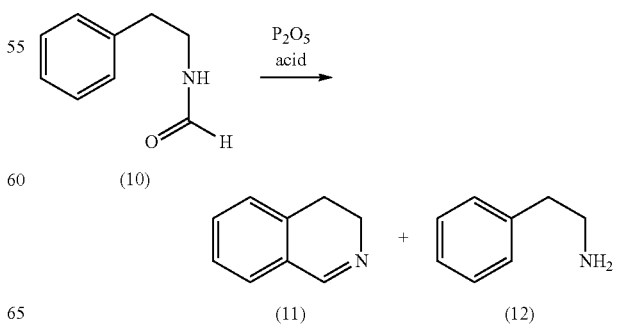

A process as described above, wherein step d) is performed using phosphorous pentoxide and an acid is another preferred object of the present invention, whereby it is preferred when the acid is selected from the group consisting of poly phosphorous acid, trifluoro methane acid, formic acid and methane sulfonic acid. Compared to standard Bischler-Napieralski reaction conditions the amount of phosphor-containing compounds as well as the reaction time could be reduced. This makes the reaction less expensive and has a positive effect with respect to the overall environmental rating of the process. Instead of poly phosphorous acid (PPA) methane sulfonic acid (MSA) can be used. This is not possible when using MSA alone. At temperatures of about 160° C., which is above the decomposition temperature of MSA, which is about 140° C., good results can be obtained.

It is further preferred when in the process as described above the reaction mixture of step d) is neutralized using KOH, because this leads to salts that have a higher solubility.

An alternative for this step is

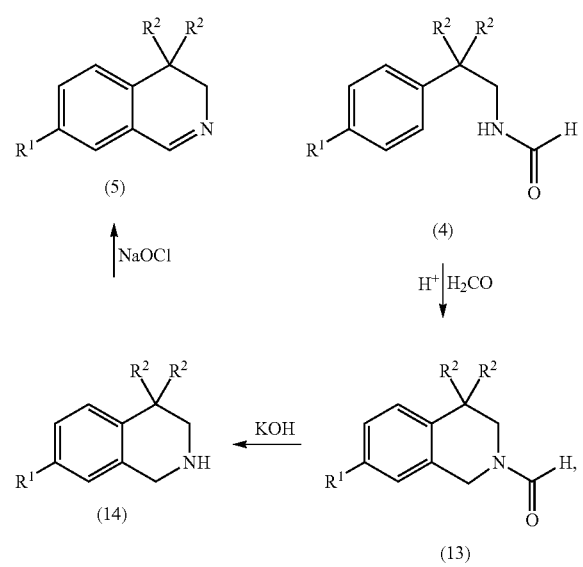

to perform a Pictet-Spengler reaction from (4) to (13), followed by cleavage of the amide to give (14) and subsequent oxidation using sodium hypochlorite. A great advantage of this alternative is to be seen in the fact that the reaction can be performed as a one pot reaction. An additional advantage is the fact, that this is a phosphate free route to obtain the desired products, which means lower cost for waste disposal and an environmentally friendly process.

As a source of formaldehyde trioxane is advantageous, since it has a melting point of 62° C., and therefore can be applied easily as a liquid. It is obvious that a heated feed pipe can advantageously been used. As the acid all kinds of strong acids, such as trifluoro acetic acid, formic acid or methane sulfonic acid can be used.

A process as described above, wherein in step d) after neutralization the amine is oxidized to give an imine using sodium hypochlorite is preferred and it is even more preferred when in this step the alkylating agent is used in an amount of 1 to 1.2 equivalents based on the product from step d):

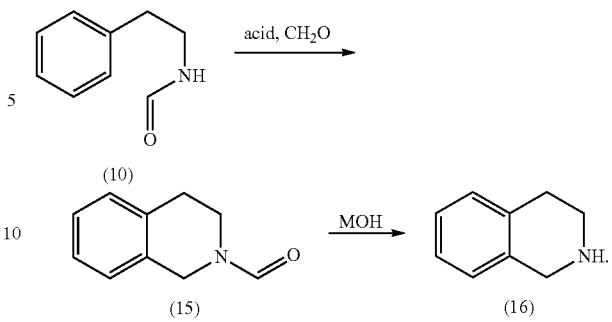

It is particularly preferred, when a process as described above is performed in which process in at least one of steps a) to e) a solvent is used, whereby preferably the same solvent is used in more than one step.

A process as described above, wherein the solvent is toluene is particularly preferred and a process wherein the solvent in steps a) to d) is toluene and in step e) is acetone or acetonitrile is most preferred. Acetone has the additional advantage of having a low boiling point—which facilitates the removal of the solvent.

Suitable organic catalysts can be produced using a variety of reaction vessels and processes including batch, semi-batch and continuous processes.

The oxaziridinium ring containing version of the aforementioned catalyst may be produced by contacting an iminium containing version of said catalyst with an oxygen transfer agent such as a peroxycarboxylic acid or a peroxymonosulfuric acid. Such species can be formed in situ and used without purification.

For a better understanding the present invention is illustrated by the following examples, which are not to be understood as being limiting the scope of the invention, which scope is expressed in the claims:

EXAMPLE 1 a) In 2 l four necked flask benzylcyanide (118 g, 1.0 mol, 1.0 eq.), 4-methyl-benzylchloride (286 g, 2.0 mol, 2.0 eq.) and toluene (510 g) were mixed. At 25° C. potassium tert-bu-tylate (288 g, 2.52 mol, 2.52 eq.) were added while stirring. After stirring for 3.5 h at 25° C. water (550 g) was added and the mixture was stirred for another 10 min. Phase separation and washing of the organic phase with water (200 g) lead—after removal of the solvent—to bisalkylated benzylcyanide (315 g, 95% of theory), having a purity of 98% according to gas chromatography (GC).

b) Bisalkylated benzylcyanide (50 g, 0.15 mol, 1.0 eq.) were dissolved in 50 g of toluene and 10 g Raney-nickel were added. After hydration in an autoclave for 25 h at a pressure of 65 bar hydrogen pressure at 100° C. the reaction was completed. Filtering off the Raney-nickel and removal of the solvent yielded the desired amine (49 g, 99% of theory) having a purity of 95% according to GC.

c) The primary amine (74 g, 0.22 mol) was treated with formic acid methyl ester (70 g, 1.17 mol) at a temperature of 25° C. for 10 h. After removal of the solvent the desired amide was obtained as a white solid (78 g, 97% of theory).

d) Phosphorous pentoxide (33 g, 0.22 mol) and poly phosphorous acid (114 g) were stirred under nitrogen atmosphere at 150° C. for 1 h. The amide (78 g, 0.22 mol) was added and the reaction mixture was stirred for 1 h at 170° C. After cooling to 80° C. water (150 g) was added, and neutralization was conducted using KOH (50% ic in water). Addition of tert-butylmethylether (600 ml), phase separation and drying of the organic phase yielded—after removal of the solvent—the 4,4-disubstituted dihydroisoquinoline (60 g, 80% of theory) having a purity of 91% according to GC.

e) The 4,4-disubstituted dihydroisoquinoline of step d) (50 g, 91% purity, 0.134 mol, 1.0 eq.) was dissolved in acetonitrile (280 ml) and propanesulton (18 g, 0.147 mol, 1.1 eq.) were added. The mixture was stirred for 2 h at a temperature of 50° C. After cooling to 25° C. and addition of tert-butylmethylether (200 ml) the desired product precipitated. After drying of the solid the aimed compound was obtained as a beige powder (47 g, 76% of theory).

EXAMPLE 2 TO 26

The following reaction was performed using various conditions:

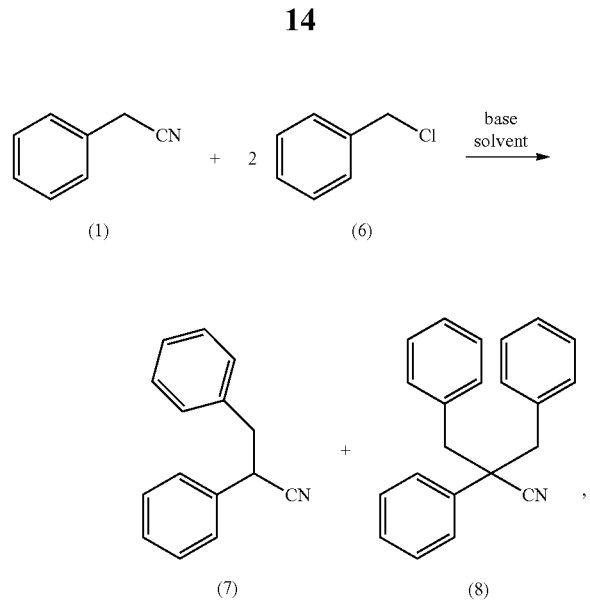

with the conditions and results being listed in table 1.

TABLE 1

| | | starting material 13 g benzyl cyanide (1) | | | | | | | |
|---|---|---|---|---|---|---|---|---|---|
| | amount | | | | | | GC [%] | | |
| Example | 2 | base | solvent | temperature | time | 1 | 6 | 7 | 8 |
| 2 | 4eq. | 3.26eq KOtBu | 78 g DMSO | RT | 20 h | 4 | 20 | 11 | 61 |
| 3 | 4eq. | 3.26eq KOtBu | 78 g THF | RT | 20 h | 15 | 24 | 2 | 58 |
| 4 | 2eq. | 3.26eq KOtBu | 78 g DMSO | RT | 4 h | | | | 87 |
| 5 | 2eq. | 3.26eq KOtBu | 40 g DMSO | RT | 4 h | | | | 92 |
| 6 | 2eq. | 3.26eq KOtBu | 40 g toluene | RT | 4 h | | | | >95 |
| 7 | 2eq. | 2eq KOtBu | 40 g toluene | RT | 4 h | | 5 | 10 | 86 |
| 8 | 2eq. | 3.26eq. NaOMe | 40 g toluene | RT | 20 h | 13 | 38 | 32 | 17 |
| 9 | 2eq. | 3.26eq. NaOMe | 40 g toluene | 60° C. | 2 h | 11 | 31 | 36 | 22 |
| 10 | 2eq. | 3.26eq. NaOMe | 40 g toluene | 100° C. | 2 h | 11 | 31 | 35 | 23 |
| 11 | 2eq. | 3.26eq. NaOMe | 40 g toluene | 100° C. | 4 h | 17 | 40 | 29 | 7 |
| 12 | 2eq. | 3.26eq. NaOMe | 40 g THF | RT | 20 h | 16 | 43 | 29 | 10 |
| 13 | 2eq. | 3.26eq. NaOMe | 40 g DMSO | RT | 4 h | 12 | 33 | 23 | 32 |
| 14 | 2eq. | 3.26eq. NaOMe | 40 g DMSO | 100° C. | 4 h | 14 | 19 | 19 | 38 |
| 15 | 2eq. | 3.26eq. NaOMe | 40 g DMSO | 100° C. | 7 h | 15 | 16 | 20 | 40 |
| 16 | 2eq. | 3.26eq. NaOMe-solution | none | RT | 20 h | 26 | 57 | 15 | 2 |
| 17 | 2eq. | 3.26eq. NaOMe-solution | none | 70° C. | 2 h | 16 | 62 | 16 | 6 |
| 18 | 2eq. | 3.26eq. NaOMe-solution | none | 86° C. | 2 h | 15 | 59 | 15 | 6 |
| 19 | 2eq. | 3.26eq. NaOMe-solution | 40 g toluene | 100° C. | 4 h | 24 | 76 | | |
| 20 | 2eq. | 3.26eq. NaOnBu-solution | none | RT | 3 h | 20 | 29 | 16 | |
| 21 | 2eq. | 3.26eq. NaOnBu-solution | none | 100° C. | 4 h | 12 | | 20 | 4 |
| 22 | 2eq. | 3.26eq. K$_2$CO$_3$ | 40 g DMF | 116° C. | 2 h | | | 48 | 38 |
| 23 | 2eq. | 3.26eq. K$_2$CO$_3$ | 40 g toluene | 116° C. | 2 h | 32 | 62 | 5 | |
| 24 | 2eq. | 3.26eq. K$_2$CO$_3$ | 40 g DMSO | 120° C. | 2 h | 13 | 2 | 32 | 8 |
| 25 | 2eq. | 3.26eq. K$_2$CO$_3$ | 40 g DMSO | 60° C. | 2 h | 20 | 46 | 28 | 7 |
| 26 | 2eq. | 3.26eq. K$_2$CO$_3$ | 40 g THF | 80° C. | 4 h | 28 | 58 | 14 | |

EXAMPLES 27 TO 46

Also the following reaction step was varied:

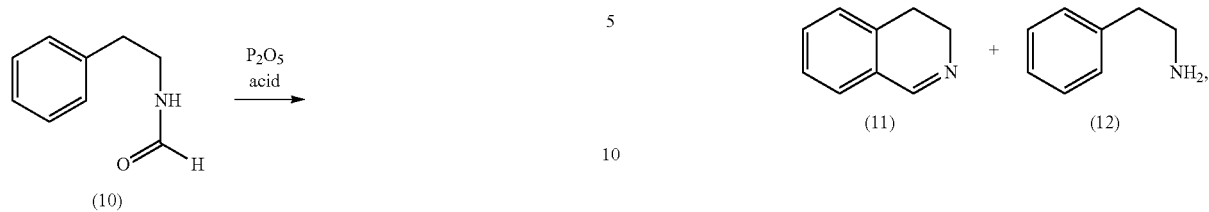

(10)

the conditions and results being listed in table 2 below:

TABLE 2

| | | | | | | GC [%] | | |
|---|---|---|---|---|---|---|---|---|
| | | | starting material 30 g (10) | | | | | |
| Example | $P_2O_5$ | acid | solvent | temperature | time | 10 | 11 | 12 |
| 27 | 36 g | 200 g PPA | none | 170° C. | 40 min. | | 99 | |
| 28 | 18 g | 100 g PPA | none | 170° C. | 40 min. | 7 | 91 | |
| 29 | 18 g | 100 g PPA | none | 170° C. | 60 min. | 4 | 95 | |
| 30 | 18 g | 100 g PPA | none | 170° C. | 60 min. | 3 | 92 | 4 |
| 31 | 18 g | 100 g PPA | none | 200° C. | 60 min. | | 95 | 5 |
| 32 | 18 g | 100 g PPA | none | 170° C. | 80 min. | 4 | 92 | 4 |
| 33 | 18 g | 100 g PPA | none | 170° C. | 120 min. | 1 | 94 | 4 |
| 34 | 18 g | 50 g PPA, 50 g MSA | none | 170° C. | 40 min. | 31 | 36 | 1 |
| 35 | 9 g | 50 g PPA | none | 170° C. | 40 min. | 21 | 30 | 20 |
| 36 | 9 g | 50 g PPA | none | 200° C. | 40 min. | | 76 | |
| 37 | 9 g | 50 g PPA | dichlorobenzene | 170-180° C. | 40 min. | 40 | 34 | 18 |
| 38 | none | 1eq. MSA | dichlorobenzene | 170° C. | 60 min. | | | 46 |
| 39 | 18 g | 180 g MSA | none | 130° C. | 3 h | 12 | 80 | 2 |
| 40 | 18 g | 72 g MSA | none | 130° C. | 3 h | 7 | 49 | 19 |
| 41 | 18 g | 180 g MSA | none | 115° C. | 24 h | 22 | 78 | |
| 42 | 18 g | 180 g MSA | none | 140° C. | 3 h | 16 | 69 | 2 |
| 43 | 18 g | 180 g MSA | none | 150-160° C. | 2 h | | 91 | |
| 44 | 18 g | 90 g MSA | none | 160° C. | 2 h | | >90 | |
| 45 | 30 g | 300 g MSA | none | 130° C. | 4 h | 6 | 81 | 1 |
| 46 | 36 g | 200 g formic acid | none | reflux | 4 h | 100 | | |

EXAMPLES 47 TO 65

The following reaction step was also object of further experiments, which are summarized in table 3 below:

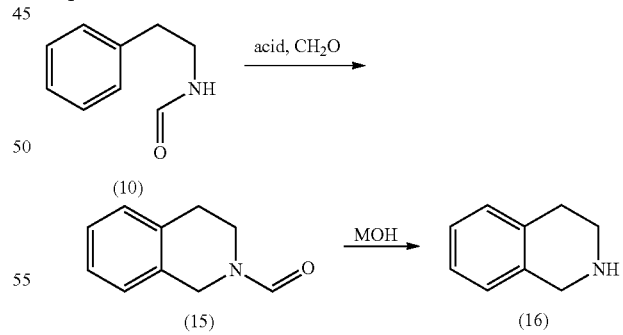

TABLE 3

| | | | 33 g starting material (10) | | | | GC [%] | |
|---|---|---|---|---|---|---|---|---|
| Example | CH2O | solvent | acid | temperature | time | 10 | 15 | 16 |
| 47 | 8 g paraformaldehyde | none | 220 ml TFA | reflux | 4.5 h | | 97 | |

TABLE 3-continued 33 g starting material (10)

| Example | CH2O | solvent | acid | temperature | time | GC [%] 10 | GC [%] 15 | GC [%] 16 |
|---|---|---|---|---|---|---|---|---|
| 48 | 8 g paraformaldehyde | none | 100 ml TFA | reflux | 4.5 h |  | 99 |  |
| 49 | 8 g paraformaldehyde | none | 75 ml TFA | reflux | 4.5 h |  | 62 | 32 |
| 50 | 8 g paraformaldehyde | none | 50 ml TFA | reflux | 4.5 h |  | 62 | 35 |
| 51 | 8 g paraformaldehyde | none | 50 ml TFA | reflux | 4.5 h |  | 56 | 30 |
| 52 | 8 g paraformaldehyde | none | 25 ml TFA | reflux | 4.5 h | 4 | 32 | 23 |
| 53 | 8 g paraformaldehyde | none | 100 ml formic acid | reflux | 4.5 h | 9 | 88 | 2 |
| 54 | 8 g paraformaldehyde | none | 100 ml propionic acid | reflux | 4.5 h | 56 |  |  |
| 55 | 8 g paraformaldehyde | Cl(CH2)2Cl | 1eq. MSA | reflux | 4.5 h | 1 | 95 |  |
| 56 | 8 g paraformaldehyde | Cl(CH2)2Cl | 1eq. MSA | reflux | 4.5 h |  | 95 |  |
| 57 | 20 g trioxane | none | 50 ml TFA | reflux | 4.5 h |  | 61 | 25 |
| 58 | 20 g trioxane | none | 50 ml TFA | reflux | 4.5 h |  | 52 | 38 |
| 59 | 20 g trioxane | none | 100 ml formic acid | reflux | 4.5 h |  | 85 | 12 |
| 60 | 20 g trioxane | none | 50 ml TFA | reflux | 4.5 h |  | 63 | 34 |
| 61 | 20 g trioxane base | none solvent | 50 ml formic acid | reflux | 5 h | 15 | 65 | 6 |
| 62 | 4eq. KOH | 150 ml ethanol |  | reflux | 2.3 h |  |  | 99 |
| 63 | 4eq. KOH | none |  | reflux | 3.5 h |  | 1 | 97 |
| 64 | 1.5eq. NaOH | none |  | 100° C. | 5 h |  | 71 | 23 |
| 65 | 1.5eq. NaOH | none |  | 100° C. | 13.5 h |  | 38 | 49 |

Besides the variation of solvents, temperatures and other reaction conditions also the educts have been varied as is shown in the following examples:

Unless otherwise indicated, materials can be obtained from Aldrich, P.O. Box 2060, Milwaukee, Wis. 53201, USA.

EXAMPLE 66

Preparation of 3,4-dihydro-4,4-dibenzyl-2-(3-sulfopropyl)isoquinolinium, Internal salt

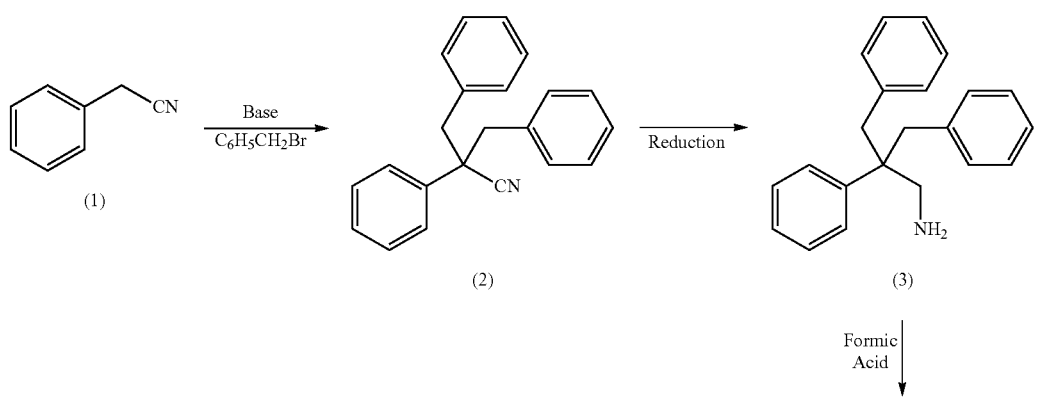

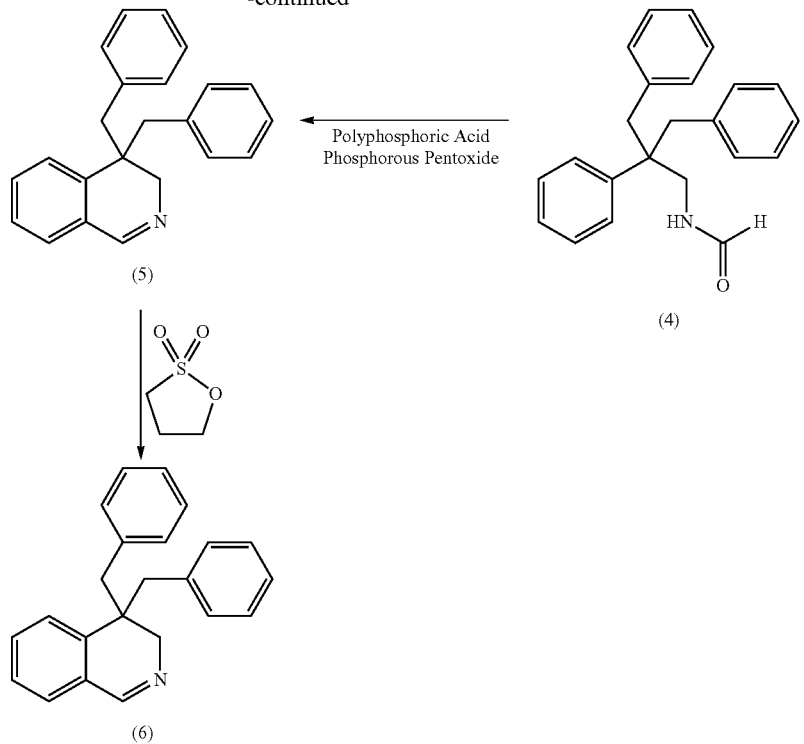

Step 1

Preparation of α,α-dibutyl-benzeneacetonitrile (2): To a flame dried 500 ml three neck round bottomed flask, equipped with a dry argon inlet, magnetic stir bar, and thermometer, is added benzyl cyanide ((1), 5.0 gm.; 0.043 mol) and tetrahydrofuran (100 ml). To the reaction is slowly added sodium hydride (60% in oil) (7.2 gm, 0.1075 mol) over one hour. Once addition is complete the reaction is stirred at room temperature for 1 hour. To the reaction is added benzyl bromide (18.4 gm; 0.043 mol) and the reaction is stirred at 50° C. for 18 hours. The reaction is evaporated to dryness, residue dissolved in toluene and washed with 1N HCl. Organic phase is dried with $Na_2SO_4$, filtered and evaporated to yield α,α-dibutyl-benzenacetonitrile (2), wt=7.7 gm (65%).

Step 2

Preparation of 1-amino-2,2,dibutyl-2-phenylethane (3): α,α-Dibutyl-benzeneacetonitrile ((2), 7.0 gm; 0.0237 mol) is dissolved in borane-THF complex (1.1 equiv.) at room temperature for 18 hours. Once reaction is complete, ethanol (50 ml) is added, and the reaction is evaporated to dryness. Once dry, the residue is suspended in 100 ml 1M HCl, and the suspension is evaporated to dryness on a rotary evaporator. This procedure is repeated three times. After the final evaporation, the white residue is dissolved in 1M NaOH (100 ml), and extracted with diethyl ether (2×150 ml). The extracts are combined, dried with $Na_2SO_4$, filtered and evaporated to dryness to yield 1-amino-2,2-dibutyl-2-phenylethane (3), wt=6.4 gm (90%).

Step 3.

Preparation of 3,4-dihydro-4,4-dibenzyl-isoquinoline (5): To a flame dried 100 ml three neck round bottomed flask, equipped with an addition funnel, dry argon inlet, magnetic stir bar, thermometer, Dean Stark trap, and heating bath is added 1-amino-2,2-dibutyl-2-phenylethane ((3), 5.0 gm, 0.0166 mol) and toluene (25 ml). To the addition funnel is added formic acid (5.0 gm). The formic acid is added slowly to the stirring reaction solution over 60 minutes and solids form. Once addition is complete the reaction is brought to reflux and water removed via a Dean Stark trap. Once the reaction is complete, the toluene is removed to yield N-formyl-β,β-dibutyl-β-phenethylamine (4), wt=4.9 gm (90%). The formamide (4) is then contacted with polyphosphoric acid (30 gm)/phosphorous pentoxide (6 gm), using standard Bischler/Napieralski conditions, at 170° C. for 18 hours. The reaction is then neutralized with aqueous NaOH, keeping the temperature between 60-80° C. Once neutral, the product is extracted with toluene to yield 3,4-dihydro-4,4-dibenzyl-isoquinoline (5). The product can be further purified on silica gel.

Step 4.

Preparation of 3,4-dihydro-4,4-dibutyl-2-(3-sulfopropyl)isoquinolinium, internal salt (6)

To a flame dried 100 ml round bottomed flask is added 3,4-dihydro-4,4-di-benzylisoquinoline ((5) 3.0 gm; 0.010 mol) and acetonitrile (25 ml). The solution is stirred at room temperature under argon and to the solution is added 1,2-oxathiolane-2,2-dioxide (1.34 gm; 0.011 mol). The reaction is warmed to 50° C. and stirred for 18 hours. The reaction is cooled to room temperature, and allowed to stand at room temperature over night. The formed solids are collected by filtration, and washed with chilled acetonitrile, to yield 3,4-dihydro-4,4-dibenzyl-2-(3-sulfopropyl)isoquinolinium (6).

EXAMPLE 67

Preparation of 3,4-dihydro-4,4-dipentyl-2-(3-sulfopropyl)isoquinolinium, internal salt The desired product is prepared according to Example 66, substituting pentyl chloride for benzyl chloride in Step 1.

EXAMPLE 68

Preparation of 3,4-dihydro-4,4-dihexyl-2-(3-sulfopropyl)isoquinolinium, internal salt The desired product is prepared according to Example 66, substituting hexyl chloride for benzyl chloride in Step 1.

EXAMPLE 69

Preparation of 3,4-dihydro-4,4-dibutyl-2-(3-sulfopropyl)isoquinolinium, internal salt The desired product is prepared according to Example 66, substituting butyl chloride for benzyl chloride in Step 1.

EXAMPLE 70

Preparation of 3,4-dihydro-4,4-di(2-methylphenylmethyl)-2-(3-sulfopropyl)-isoquinolinium, internal salt The desired product is prepared according to Example 66, substituting 2-methylbenzyl chloride for benzyl chloride in Step 1.

EXAMPLE 71

Preparation of 3,4-dihydro-4,4-di(3-methylphenylmethyl)-2-(3-sulfopropyl)-isoquinolinium, internal salt The desired product is prepared according to Example 66, substituting 3-methylbenzyl chloride for benzyl chloride in Step 1.

EXAMPLE 72

Preparation of 3,4-dihydro-4,4-di(4-methylphenylmethyl)-2-(3-sulfopropyl)-isoquinolinium, internal salt The desired product is prepared according to Example 66, substituting 4-methylbenzyl chloride for benzyl chloride in Step 1.

EXAMPLE 73

Preparation of 3,4-dihydro-4,4-di(cyclohexylmethyl)-2-(3-sulfopropyl)-isoquinolinium, internal salt The desired product is prepared according to Example 66, substituting chloromethyl cyclohexane (prepared from cyclohexanemethanol according to Coe et al., Polyhedron 1992, 11(24), pp. 3123-8) for benzyl chloride in Step 1.

EXAMPLE 74

Preparation of 3,4-dihydro-4,4-di(phenylmethyl)-2-(3-sulfobutyl)-isoquinolinium, internal salt The desired product is prepared according to Example 66, substituting 1,2-oxathiane-2,2-dioxide for 1,2-oxathiolane-2,2-dioxide in Step 4.

EXAMPLE 75

Preparation of 3,4-dihydro-4,4-di(phenylmethyl)-2-[2'-(sulfooxy)ethyl]-isoquinolinium, internal salt The desired product is prepared according to Example 66, substituting 1,3,2-dioxathiolane-2,2-dioxide for 1,2-oxathiolane-2,2-dioxide in Step 4.

EXAMPLE 76

Preparation of 3,4-dihydro-4,4-di(phenylmethyl)-2-[3-(sulfooxy)propyl]-isoquinolinium, internal salt The desired product is prepared according to Example 66, substituting 1,3,2-dioxathiane-2,2-dioxide for 1,2-oxathiolane-2,2-dioxide in Step 4.

EXAMPLE 77

Preparation of 3,4-dihydro-4,4-di(4-methyl phenylmethyl)-7-methyl-2-(3-sulfopropyl)-isoquinolinium, internal salt Step 1:

Preparation of 4-Methyl-α-(4-methylphenyl)-α-[(4-methylphenyl)methyl]-benzenepropanenitrile Part a.
Preparation of silica catalyst: Silica (MKC-500, specific surface area 497 $m^2$ $g^{-1}$; obtained from Nikki Chemical) is activated by treatment with 6N HCl and dried in a vacuum at 120° C. A mixture of 7.0 g of activated silica gel and 80 ml of toluene is placed in a flask and stirred for one hour. Then, 25 ml of N-(2-aminoethyl)-3-aminopropyltrimethoxysilane (SH-6020; obtained from Troy Silicone) is injected by syringe and the resulting mixture refluxed with an oil bath for 8 h. After cooling, the silica gel is filtered and washed with benzene in a soxhlet extractor for 12 h. The purified silica is washed again three times with diethyl ether and allowed to stand overnight in air. One gram of the purified silica is then suspended in 1.5 ml of dioxane for 8 h, after which 4.3 ml of 1,10-dibromodecane is added and the mixture stirred at 80° C. overnight in an oil bath. The silica is then filtered on a glass filter and washed with dioxane, acetone and 1% $NH_4OH$ and subsequently washed with acetone and diethyl ether. The silica so obtained is dried at 50° C. under reduced pressure overnight.

Part b.
Preparation of 4-Methyl-α-(4-methylphenyl)-α-[(4-methylphenyl)methyl]-benzenepropanenitrile: A flask containing 1.0 g (2 mmol) of sodium cyanide (95%) dissolved in 5 ml of 50% NaOH aqueous solution is charged with 0.3 g silica catalyst, followed by 4-methylbenzyl chloride (6.8 mmol) and 1 ml toluene. The flask is placed in an oil bath and heated at 40° C. with stirring for 48 h, after which 10 ml toluene is added. The organic layer is filtered and the filtrate evaporated to yield 4-methyl-α-(4-methylphenyl)-α-[(4-methylphenyl)methyl]-benzenepropanenitrile.

Step 2.

Preparation of 4-methyl-α-(4-methylphenyl)-α-[(4-methylphenyl)methyl]-benzenepropanamine The desired product is prepared according to Example 66, Step 2, substituting 4-methyl-α-(4-methylphenyl)-α-[(4-methylphenyl)methyl]-benzenepropanenitrile for α,α-dibutyl-benzeneacetonitrile.

Step 3.

Preparation of 3,4-dihydro-4,4-di(4-methylphenylmethyl)-7-methyl-isoquinoline: The desired product is prepared according to Example 66, Step 3, substituting 4-methyl-α-(4-methylphenyl)-α-[(4-methylphenyl)methyl]-benzenepropanamine for 1-amino-2,2,dibutyl-2-phenylethane.

Step 4.

Preparation of 3,4-dihydro-4,4-di(4-methyl phenylmethyl)-7-methyl-2-(3-sulfopropyl)-isoquinolinium, internal salt The desired product is prepared according to Example 66, Step 4, substituting 3,4-dihydro-4,4-di(4-methylphenylmethyl)-7-methyl-isoquinoline for 3,4-dihydro-4,4-di-benzyl-isoquinoline.

EXAMPLE 78

Preparation of 3,4-dihydro-4,4-di(4-iso-propylphenylmethyl)-7-iso-propyl-2-(3-sulfopropyl)isoquinolinium, internal salt The desired product is prepared according to Example 77, substituting 4-iso-propylbenzyl chloride for 4-methylbenzyl chloride.

EXAMPLE 79

Simultaneous Preparation of Organic Catalyst Mixture Comprising Catalysts of Formula 3 Wherein $R^1$ are Independently H, Methyl, Ethyl and Mixtures Thereof

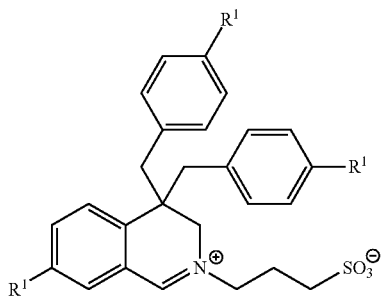

Formula 3

The desired mixture of products is prepared according to Example 77, substituting a mixture of benzyl chloride (source for $R^1$=H), 4-methylbenzyl chloride (source for $R^1$=methyl), and 4-ethylbenzyl chloride (Oakwood Products, Inc., West Columbia, S.C. 29172, USA; source for $R^1$=ethyl) for 4-methylbenzyl chloride. This results in a mixture of 18 distinct organic catalyst compounds.

EXAMPLE 80

The organic catalysts listed below are tested according to Applicants' Organic Catalyst/Enzyme Compatibility Test using [Peracetic Acid]=5.0 ppm; [organic catalyst]=0.5 ppm and the following results are obtained.

| Entry* | **Catalyst Moieties $R^2$; G | Enzyme Compatibility Values | | | |
|---|---|---|---|---|---|
| | | $ECV_{ter}$ | $ECV_{dur}$ | $ECV_{nat}$ | ECV |
| 1 | NA | 51 | 86 | 58 | 65 |
| 2 | NA | 54 | 90 | 57 | 67 |
| 3 | benzyl; —O— | 101 | 100 | 103 | 101 |
| 4 | benzyl; —CH$_2$— | 102 | 99 | 104 | 102 |
| 5 | 4-methylbenzyl; —CH$_2$— | 103 | 99 | 99 | 100 |

*Entry 1 and 2 are Sulfuric acid mono-[2-(3,4-dihydro-isoquinolin-2-yl)-1-((1,1-di-methylethoxy)methyl)ethyl] ester, internal salt and Sulfuric acid mono-[2-(3,4-dihydro-isoquinolin-2-yl)-1-(2-ethyl-hexyloxymethyl)-ethyl] ester, internal salt, respectively, which are not encompassed by Applicants' Formulae 1 and 2.
**$R^1$ is H for entries 3-5.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A process for producing a quaternized sulfo group-containing 3,4-dihydroisoquinoline, comprising
    (a) reducing a nitrile of a benzyl cyanide, to give an amine;
    (b) amidifying the amine obtained in the reducing (a), to give an amide;
    (c) ring closing the amide obtained in the amidifying (b), to give a 3,4-dihydroisoquinoline; and
    (d) quaternizing the 3,4-dihydroisoquinoline obtained in the ring closing (c) with a sulfo group-containing compound, to give a quaternized sulfo group-containing 3,4-dihydroisoquinoline,
    wherein said sulfo group-containing compound excludes thionyl chloride.

2. The process of claim 1, wherein the reducing (a) is performed with hydrogen in the presence of a catalyst.

3. The process of claim 1, wherein the amidifying (b) is performed with at least one selected from the group consisting of formic acid and formic acid ester.

4. The process of claim 1, wherein the ring closing (d) is performed with phosphorous pentoxide and an acid.

5. The process of claim 4, wherein the acid is selected from the group consisting of poly phosphorous acid, trifluoromethanesulfonic acid, formic acid, and methane sulfonic acid.

6. The process of claim 4, wherein the reaction mixture of the ring closing (c) is neutralized with KOH.

7. The process of claim 1, wherein, in the ring closing (c), after neutralization, the amine is oxidized with sodium hypochlorite to give an imine.

8. The process of claim 1, wherein, in the quaternizing (d), the alkylating agent is employed in an amount of 1 to 1.2 equivalents based on the 3,4-dihydroisoquinoline from the ring closing (c).

9. The process of claim 1, wherein, in at least one of (a) to (d), a solvent is employed.

10. The process of claim 9, wherein the same solvent is employed in more than one of (a) to (d).

11. The process of claim 9, wherein the solvent is toluene.

12. The process of claim 10, wherein the solvent is toluene.

13. The process of claim 1, further comprising:
    bisalkylating a benzyl cyanide, to give a bisalkylated benzyl cyanide, which bisalkylated benzyl cyanide is the nitrile which is reduced in the reducing (a).

14. The process of claim 13, wherein, in the bisalkylating, at least one selected from the group consisting of an alkyl chloride, alkyl bromide, alkyl iodide, alkyl tosylate, a substituted aryl chloride, substituted aryl bromide, substituted aryl iodide, and substituted aryl tosylate, is employed in amount of 2 to 4 equivalents based on the benzyl cyanide.

15. The process of claim 14, wherein in the bisalkylating, at least one selected from the group consisting of an alkyl chloride and a substituted benzyl chloride is employed in amount of 2 to 2.5 equivalents based on the benzyl cyanide.

16. The process of claim 13, wherein the bisalkylating takes place in the presence of 2 to 4 equivalents, based on the benzyl cyanide, of a base.

17. The process of claim 16, wherein the base is KOtBu or KOH/tBuOH.

18. The process of claim 13, wherein solvent, alkylating agent, and the benzyl cyanide are first mixed, and the bisalkylating is initiated by addition of base.

19. The process of claim 13, wherein, in at least one of the bisalkylating, (a) to (d), a solvent is employed.

20. The process of claim 19, wherein the same solvent is employed in more than one of the bisalkylating, (a) to (d).

21. The process of claim 1, wherein the sulfo group-containing compound is 1,2-oxathiolane-2,2-dioxide or 1,2-oxathiane-2,2-dioxide.

22. The process of claim 1, wherein the quaternized sulfo group-containing 3,4-dihydroisoquinoline is 1-(4,4-dimethyl-3,4-dihydroisoquinoline)decane-2 sulfate.

* * * * *